US011663926B2

(12) United States Patent
Kim et al.

(10) Patent No.: US 11,663,926 B2
(45) Date of Patent: *May 30, 2023

(54) SYSTEM AND METHOD FOR FOOD CATEGORIZATION

(71) Applicant: MYFITNESSPAL, INC., San Francisco, CA (US)

(72) Inventors: Joohyun Kim, San Francisco, CA (US); Chul Lee, San Francisco, CA (US); Bryan Levine, San Francisco, CA (US)

(73) Assignee: MyFitnessPal, Inc., Austin, TX (US)

( * ) Notice: Subject to any disclaimer, the term of this patent is extended or adjusted under 35 U.S.C. 154(b) by 95 days.

This patent is subject to a terminal disclaimer.

(21) Appl. No.: 16/861,901

(22) Filed: Apr. 29, 2020

(65) Prior Publication Data
US 2020/0257715 A1    Aug. 13, 2020

Related U.S. Application Data

(63) Continuation of application No. 14/513,061, filed on Oct. 13, 2014, now Pat. No. 10,671,657.

(51) Int. Cl.
*G09B 19/00* (2006.01)
*G06F 16/35* (2019.01)
*G06Q 10/10* (2023.01)
*G16H 20/60* (2018.01)

(52) U.S. Cl.
CPC ....... *G09B 19/0092* (2013.01); *G06F 16/353* (2019.01); *G06Q 10/10* (2013.01); *G16H 20/60* (2018.01); *A23V 2002/00* (2013.01)

(58) Field of Classification Search
CPC .............. G06F 19/3475; G06F 16/353; G09B 19/0092; A23V 2002/00; G06Q 10/10; G16H 20/60
See application file for complete search history.

(56) References Cited

U.S. PATENT DOCUMENTS

| | | | |
|---|---|---|---|
| 5,233,520 A | 8/1993 | Fong | |
| 5,683,251 A * | 11/1997 | Logan | G09B 29/00 273/156 |
| 5,819,735 A | 10/1998 | Kocher | |
| 6,796,507 B2 | 9/2004 | Bean | |
| 7,076,438 B1 | 7/2006 | Albertson | |

(Continued)

*Primary Examiner* — Jack Yip
(74) *Attorney, Agent, or Firm* — Maginot, Moore & Beck, LLP

(57) ABSTRACT

A method of operating a food categorization engine includes extracting features from each text description of a training food data set to generate a feature set. The feature set is analyzed to determine sets of food categorization features that correlate to one or more food categories, wherein the sets of food categorization features are defined by a plurality of category vectors. Individual words and/or characters of a text description of a food item received from a user are then analyzed in order to generate a numerical vector representative thereof. The numerical vector is multiplied by a matrix defined by the plurality of category vectors. One or more food categories with which to associate the received food item are automatically selected based at least in part on the multiplication, and the data record associated with the food item is amended to include the selected food categories.

21 Claims, 6 Drawing Sheets

(56) References Cited

U.S. PATENT DOCUMENTS

| | | |
|---|---|---|
| 9,104,943 B2 | 8/2015 | Gotoh |
| 9,311,568 B1* | 4/2016 | Feller ................. G06K 9/00469 |
| 9,734,426 B2 | 8/2017 | Divakaran |
| 2003/0091964 A1* | 5/2003 | Yeager ................... G16H 70/00 |
| | | 708/133 |
| 2007/0191689 A1* | 8/2007 | Elitok .................... G16H 20/60 |
| | | 600/300 |
| 2009/0105875 A1 | 4/2009 | Wiles |
| 2010/0216098 A1 | 8/2010 | Montgomery |
| 2011/0250320 A1 | 10/2011 | Agami |
| 2012/0005222 A1 | 1/2012 | Bhagwan |
| 2013/0105565 A1 | 5/2013 | Kamprath |
| 2013/0216982 A1 | 8/2013 | Benneii |
| 2014/0147829 A1 | 5/2014 | Jerauld |
| 2015/0132722 A1 | 5/2015 | Menczel |
| 2015/0170001 A1 | 6/2015 | Rabinovich |
| 2015/0170543 A1 | 6/2015 | Shahar |
| 2015/0228062 A1 | 8/2015 | Joshi |
| 2015/0339394 A1 | 11/2015 | Jinq |
| 2015/0347520 A1 | 12/2015 | King |
| 2016/0012749 A1 | 1/2016 | Connor |
| 2016/0063734 A1 | 3/2016 | Divakaran |
| 2016/0063888 A1 | 3/2016 | McCallum |

\* cited by examiner

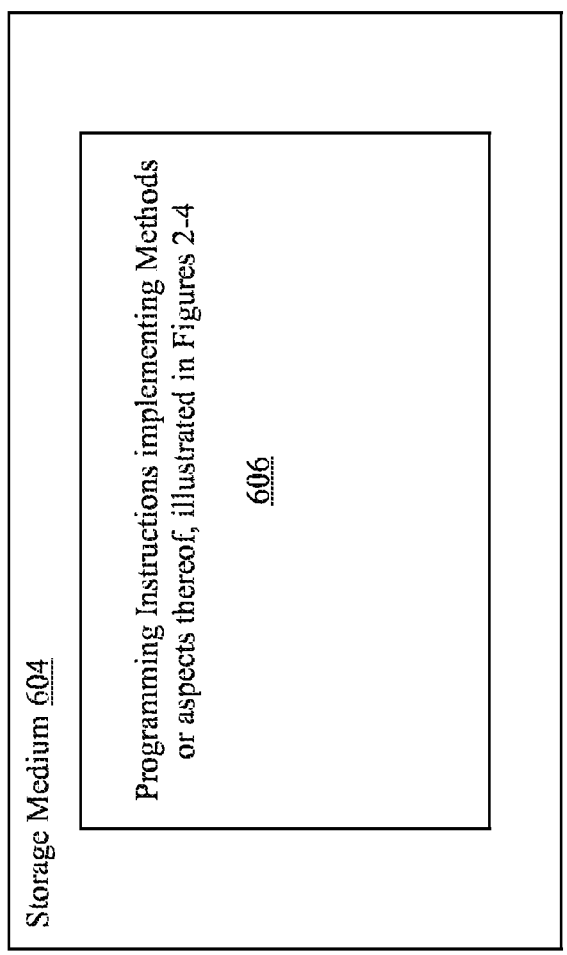

SYSTEM AND METHOD FOR FOOD CATEGORIZATION

CROSS-REFERENCE TO RELATED APPLICATIONS

This document is a continuation of U.S. patent application Ser. No. 14/513,061, filed Oct. 13, 2014, the entire contents of which are incorporated by reference herein.

FIELD

The present disclosure relates to the field of data processing. More particularly, the present disclosure relates to food item categorization.

BACKGROUND

The background description provided herein is for the purpose of generally presenting the context of the disclosure. Unless otherwise indicated herein, the materials described in this section are not prior art to the claims in this application and are not admitted to be prior art by inclusion in this section.

In monitoring a person's food and/or beverage intake it may be beneficial to categorize the food and/or beverages a user takes in. Historically, categorizing food and/or beverages may entail manual entry of any categories that may be applicable to the food and/or beverages. Such manual categorization may lead to the use of a limited number of broad food categories. In addition, the application of these broad food categories may need to be rigid due to the inability to efficiently re-categorize a large number of food and/or beverages when a change in food categories may occur.

SUMMARY

Methods and systems for operating a food categorization engine are disclosed herein. In at least one embodiment, a food categorization engine is provided on a server and operating in a training mode is configured to receive a training food data set including a plurality of text descriptions of a plurality of food items and a corresponding association of each of the plurality of food items of the training food data set with one or more food categories of a plurality of food categories, wherein the training food data set is provided from a database of crowd-sourced data records of food items. A method includes extracting, by the food categorization engine, one or more features from each text description of the training food data set to generate a feature set for each food item of the training food data set. Thereafter, the method includes analyzing, by the food categorization engine, the feature set for each food item of the training food data set to determine sets of food categorization features that correlate to individual ones of the one or more food categories, wherein the sets of food categorization features are defined by a plurality of category vectors, each of the category vectors associated with one of the food categories. The method further includes standardizing a text description of a food item received from a user of a client device in communication with the server, the food item associated with a data record in the database. Additionally, the method includes analyzing, by the food categorization engine, one or more individual words and/or characters of the text description of the food item, wherein analyzing the one or more individual words and/or characters of the text description of the food item comprises generating a numerical vector representative thereof. The method also includes multiplying the numerical vector by a matrix defined by the plurality of category vectors, automatically selecting one or more food categories with which to associate the food item based at least in part on the multiplication, and amending the data record associated with the food item in the database to include the selected one or more food categories. Furthermore, the method includes selecting the amended data record based on the one or more food categories and transmitting data from the amended data record to the user for display on the client device.

In at least one embodiment, one or more non-transitory computer-readable media are disclosed having a plurality of instructions stored thereon. The instructions, in response to execution by a processor of a network-side computing device in communication with a crowd-sourced database of data records of food items, provide the computing device with a food item categorization engine operable to receive, in a training mode, a training food data set including a plurality of text descriptions of a plurality of food items and a corresponding association of each of the plurality of food items of the training food data set with one or more food categories of a plurality of food categories. The food categorization engine is further operable to extract one or more features from each text description of the training food data set to generate a feature set for each food item of the training food data set, and analyze the feature set for each food item of the training food data set to determine sets of food categorization features that correlate to individual ones of the one or more food categories, wherein the sets of food categorization features are defined by a plurality of category vectors, each of the category vectors associated with one of the food categories. The food categorization engine is further operable to receive, in an operational mode, a data record including a text description of a food item from a client-side application configured to log consumption of food items, wherein the received data record is selected by the user as being indicative of a consumed item, the data record being provided from the database of crowd-sourced data records of food items. Additionally, the food categorization engine is operable to standardize the text description of the food item included with the received data record, analyze one or more individual words and/or characters of the text description of the food item to create a numerical vector representative thereof, and automatically select one or more food categories with which to associate the received data record and associated food item based at least in part on a result of a comparison of the numerical vector to the plurality of category vectors associated with individual ones of the one or more food categories, wherein the comparison is accomplished by matrix-vector multiplication wherein the plurality of category vectors associated with individual ones of the one or more food categories define a matrix that is multiplied by the numerical vector. The food categorization engine is further operable to amend the data record associated with the food item in the database to include the automatically selected one or more food categories, and select the amended data record based on the one or more food categories.

In yet another embodiment, a server apparatus is disclosed comprising at least one transceiver, a storage apparatus configured to store a plurality of instructions of a food categorization engine, and one or more processors configured to execute the plurality of instructions of the food categorization engine. When executed the instructions cause the server apparatus to receive, in a training mode, a training food data set including a plurality of text descriptions of a plurality of food items and a corresponding association of each of the plurality of food items of the training food data set with one or more food categories of a plurality of food categories, the training food data set provided from a database of crowd-sourced data records of food items entered into the database by a plurality of users of a fitness management system. The instructions further cause the server apparatus to extract one or more features from each text description of the training food data set to generate a feature set for each food item of the training food data set, and analyze the feature set for each food item of the training food data set to determine sets of food categorization features that correlate to individual ones of the one or more food categories, wherein the sets of food categorization features are defined by a plurality of category vectors, each of the category vectors associated with one of the food categories. The instructions further cause the server apparatus to receive, in an operational mode, at the transceiver an input from a client device comprising a data record including a description of a food item, wherein the received data record is indicative of a consumed item, the data record being provided from the database of crowd-sourced data records. Additionally, the instructions cause the server apparatus to standardize the description of the food item to create a plurality of tokens representative of one or more individual words and/or characters thereof, convert the plurality tokens to a numerical vector, and compare the numerical vector to a plurality of sets of the plurality of category vectors, each set being associated to a respective one of a plurality of food categories, wherein said comparison is accomplished by matrix-vector multiplication wherein the plurality of category vectors define a matrix that is multiplied by the numerical vector. Based on the comparison, the instructions then cause the server apparatus to identify a one of the plurality of food categories associated to a one of the plurality of sets of the plurality of category vectors to which the numerical vector matches within a predetermined threshold, amend the data record to include the identified one of a plurality of food categories, the data record associated with the description of the food item in the database, and select the amended data record from the database based on the identified one of the plurality of food categories.

The above described features and advantages, as well as others, will become more readily apparent to those of ordinary skill in the art by reference to the following detailed description and accompanying drawings. While it would be desirable to provide a method and system for food categorization that provides one or more of these or other advantageous features as may be apparent to those reviewing this disclosure, the teachings disclosed herein extend to those embodiments which fall within the scope of the appended claims, regardless of whether they include or accomplish one or more of the advantages or features mentioned herein.

BRIEF DESCRIPTION OF THE DRAWINGS

FIG. 6 illustrates an example storage medium having instructions to cause a computing device to practice aspects of food item categorization, in accordance with various embodiments.

DESCRIPTION

Figure 1:
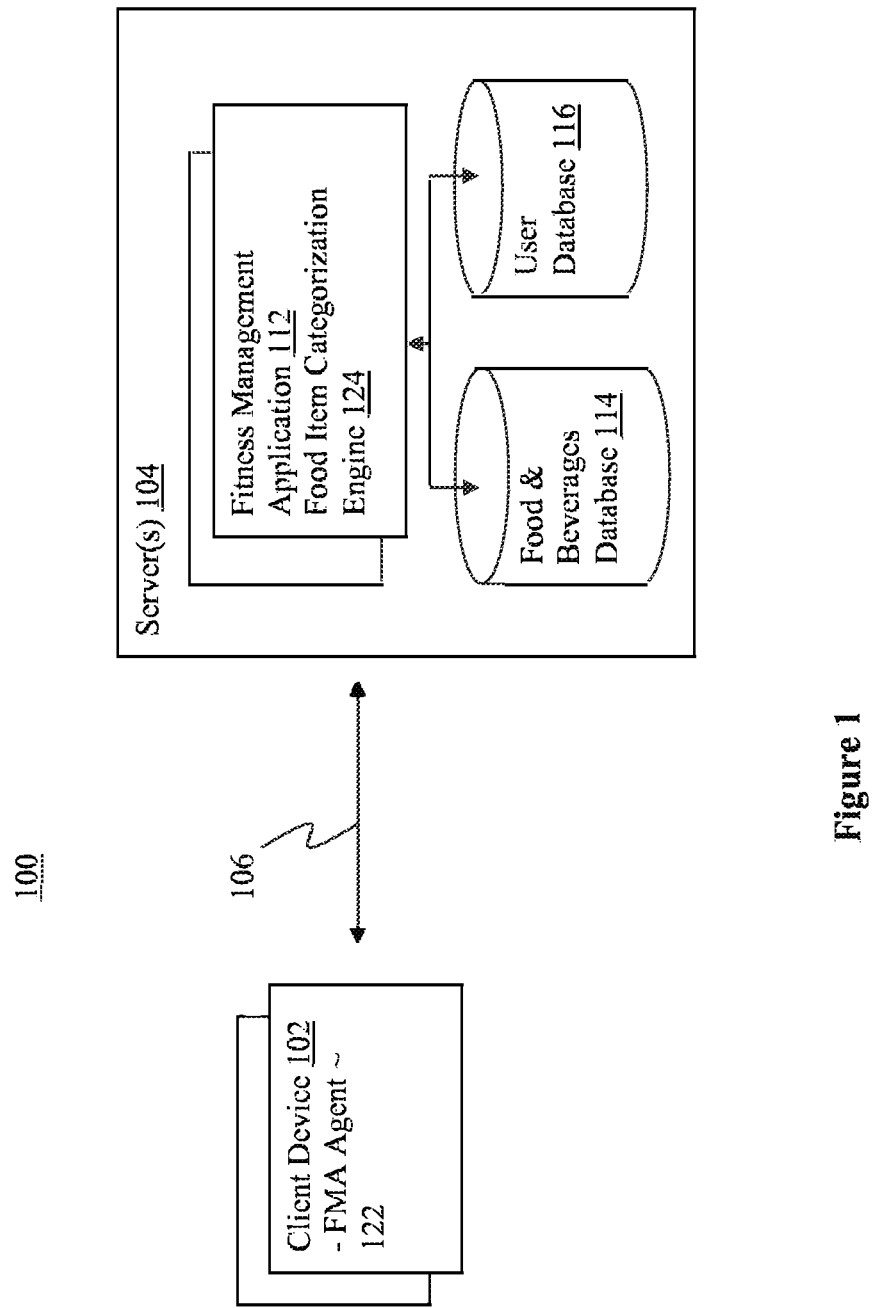
FIG. 1 illustrates a fitness management system suitable for practicing the present disclosure, in accordance with various embodiments.

Disclosed embodiments include apparatuses, methods and storage media associated with food item categorization.

In the following detailed description, reference is made to the accompanying drawings which form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that like elements disclosed below are indicated by like reference numbers in the drawings.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

Referring now to FIG. 1, wherein a fitness management system, according to the various embodiments, is illustrated. As shown, fitness management system (EMS) 100 may include any number of client devices (e.g., client device 102) and one or more server(s) 104 coupled with each other. Server(s) 104 may host a fitness management application (FMA) 112, including a number of databases, e.g., food and beverages database 114 and user database 116, configured in accordance with the teachings of the present disclosure. Whereas client device 102 may include a client side agent 122 of FMA 112 configured to access and interact with FMA 112, to enable a user of the client device 102, among other things, to develop a fitness plan that may include a nutritional, or food and beverage, budget, and monitor the progress towards meeting the fitness plan. For example, a user may develop a fitness plan including a caloric budget designating a number of calories the user would like to consume in a day. For those attempting to lose weight the designated number of calories may be a maximum number the user may like to stay below, while, for those looking to gain weight, the designated number of calories may be a minimum number of calories the user may like to stay above.

In some embodiments, the user may be able to further designate various food categories for these calories. For example, in some embodiments, the user may be able to designate a number of the user's budgeted calories that may be utilized towards various different food categories. These categories may be broad food categories (e.g., fruit, vegetable, dairy, grain, meat, etc.) or may be more granular (e.g., egg, cheese, bread, cereal, rice, pasta, poultry, beef, pork, bean, nuts, herb, spice, condiment, etc.). It will be appreciated that these categories are merely meant to be illustrative of possible food categories, food categories may be broader or more granular than the examples given above without departing from the scope of the present disclosure. In other embodiments, a user may be able to designate a nutritional source of the calories, for example, if a user would like to limit the user's caloric intake from fat, the user may designate a maximum budget of the user's calories from fat. As another example, if the user is looking to gain or maintain muscle mass the user may designate a minimum budget of the user's caloric intake that should come from proteins. It will be appreciated that these examples of fat and protein may also be included as different food categories, in addition to being the nutritional source of calories associated with various food items.

Once such a fitness plan is developed, the user may utilize client side agent 122, in conjunction with FMA 112, to monitor the user's intake of foods and/or beverages. This may be accomplished by the user entering individual food and/or beverage items that the user consumes along with quantities of these food and/or beverage items consumed. In some instances the food and/or beverage item may already have a food record in food and beverages database 114. In such instances, the user may merely select the food and/or beverage item from a list of food and/or beverage items and then enter quantity consume. FMA agent 122, in conjunction with FMA 112, may then be configured to incorporate the consumption of the food and/or beverage item into the user's nutritional budget based upon a description of the food item in the food record of the food and beverages database 114 along with any food categories associated with the food item. Such a food record may include nutritional information, such as that discussed below. In some instances the food and/or beverage item may not have an existing record, or the user may not be able to find the appropriate food record for the food and/or beverage item. In such instances, the user may enter the information that the user knows about the food including a food identifier, brand name, country of origin, a description including any nutritional information the user knows, and any additional description the user would like to enter for the food.

In some embodiments, the user may also select one or more existing food categories and/or enter one or more new food categories with which to associate the food and/or beverage item when entering the above mentioned information. Food item categorization engine 124 may also be configured to identify one or more additional food categories with which to associate the food and/or beverage item through an automated selection of food categories by extracting features of the description and utilizing the features to identify the one or more additional food categories with which to associate the food and/or beverage item, a more detailed description of such a process is discussed further below. In embodiments, food item categorization engine 124 may be configured to utilize the one or more food categories selected and/or entered by the user to refine, or train, the automated selection of food categories based on feature extraction of the description, such as that described below. In other embodiments, the user may not enter any food categories with which to associate the food and/or beverage item and the food item categorization may be configured to automatically select one or more food and/or beverage categories by extracting features of the description and utilizing the features to identify the one or more food and/or beverage categories with which to associate the food and/or beverage item, a more detailed description of such a process is discussed further below. In some embodiments, any food and/or beverage categories associated with the food and/or beverage item may then be incorporated into the user's nutritional budget where the user has designated any food and/or beverage category restrictions. In some embodiments, the food and/or beverage categories may also be used, for example by FMA 112, to generate a report depicting the food and/or beverage categories from which the user has consumed any food and/or beverage items. Such a report may give the user a better idea of the user's eating and/or drinking habits.

In embodiments, server(s) 104, except for FMA 112 and databases 114-116, may be any one of a number of computer servers, real or virtual, known in the art, including, but not limited to, servers available from Dell Computing of Austin, Tex. or Hewlett Packard of Palo Alto, Calif. In embodiments, FMA 112 may include food item categorization engine 124, hereinafter referred to simply as "categorization engine 124." Whereas food & beverages database 114 may include food and beverage items, including a description of the food and beverage items that may include nutrient information associated with the food and beverage items, as well as recipes and ingredient items. Examples of nutrient information may include, but are not limited to, amounts of protein; sugar; various fats, including trans-fat, saturated fat, etc.; sodium; carbohydrates, both complex and simple; calcium, various vitamins and/or calories per serving. In some embodiments, server(s) 104 may represent a cloud computing environment where each of FMA 112, categorization engine 124, food and beverages database 114, and user database 116 may reside, individually or in any combination, on servers, real or virtual, of the cloud computing environment.

In embodiments, client device 102 may be any one of a number of stationary or portable electronic devices known in the art, including, but not limited to, desktop computers (e.g. those available from Dell Computing of Austin, Tex.), smartphones, computing tablets, laptop computers, electronic readers, personal digital assistants, and so forth, such as Galaxy S4 from Samsung Electronics of Seoul, Korea, or iPad from Apple Computer of Cupertino, Calif. In embodiments, one or more portable computing devices 102 may be a wearable computing device, e.g., a smart watch, smart eyeglasses (e.g., Google Glass from Google of Mountain View, Calif.), and so forth. In embodiments, FMA agent 122 may be a web-based application configured to operate in a generic browser, such as Internet Explorer, available from Microsoft Corp., of Redmond, Wash., or Safari from Apple Computer of Cupertino, Calif. In other embodiments, FMA agent 122 may be a stand-alone client side application, e.g., a mobile app configured to run on a smartphone such as, for example, a mobile app available through the App Store from Apple Computer of Cupertino, Calif.

In embodiments, client device 102 and server(s) 104 may be communicatively coupled with one another via communication link 106 over one or more wired and/or wireless, private and/or public networks, including the Internet. Client device 102 and server(s) 104 may be configured with the appropriate networking communication interfaces. An example of a wired communication interface may include, but is not limited to, Ethernet, while examples of wireless communication interfaces may include, but are not limited to, near field communication (NFC), Bluetooth, WiFi, 4G or 5G LTE. In between the communication interfaces of client devices 102 and server(s) 104 may be any number of gateways, routers, switches, based stations, and so forth.

For ease of description, hereinafter, including the claims, the term "food" will be used to mean "food and/or beverage," unless the context clearly indicates otherwise.

Figure 2:
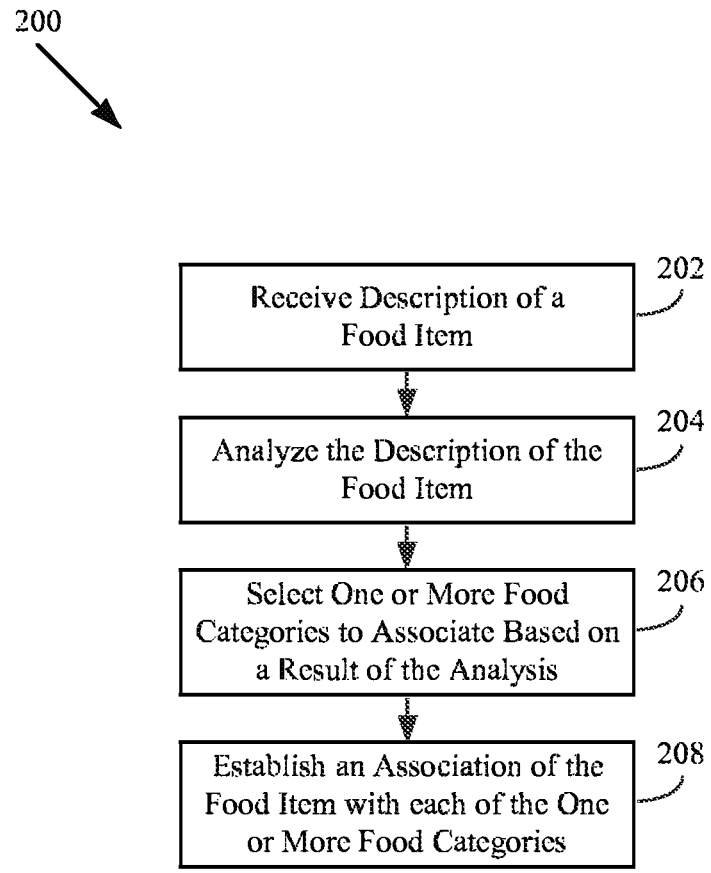
FIG. 2 illustrates example operation flow of food item categorization, in accordance with various embodiments.

FIG. 2 illustrates an example operation flow 200 for food item categorization, in accordance with various embodiments of the present disclosure. In embodiments, categorization engine 124 of FIG. 1 may be configured to perform all of or any portion of, operation flow 200 in an operational phase. Operation flow 200 may begin at block 202 where the description of the food item may be received by the categorization engine. Such a description may be received by the categorization engine, for example, from FMA agent 122 of client device 102 of FIG. 1 via communication link 106 of FIG. 1. As discussed above in reference to FIG. 1, the description may be entered by a user of computing device 102, for example, to describe a food item that the user consumed to be incorporated into a fitness plan the user developed.

At block 204, the categorization engine may analyze the description of the food item. In some embodiments, the analysis may include a data standardization process performed on the description. In embodiments this may be accomplished by the categorization engine tokenizing the description. As used herein, tokenizing may refer to the process of dividing the text of the description into smaller components, or tokens, to be processed. The tokens may be individual characters, words, groups of words (e.g., every three words), or groups of characters (e.g., every five characters).

Once the description has been tokenized it may be processed by the categorization engine to standardize the description. Such a standardization process may include the removal of stop words designated, for example, by a list of stop words contained within a table of the food and beverages database. The standardization may also include the removal of punctuation or special characters from the description. In addition, the standardization process may include: the removal of traditional stop words (e.g., a, the, etc.); the removal of numeric words from the food item description (e.g., one, two, three, etc.); removal of words related to quantities from the food item description (e.g., cup, ounce, etc.); and/or removal of food related stop words (e.g., calorie, breakfast, lunch, etc.). In some embodiments, the standardization may also include removal of "bad" keywords that may be defined, for example, in a table of bad keywords stored in the food and beverages database. Such bad keywords may be for example, profanities, vulgarities, etc. In still further embodiments, the standardization may include removal of non-English characters from the food item description and/or replacement of non-English characters with the closest English equivalent. For example, the 'ñ' jalapeno may be replaced by an English 'n,'

Once the description has been standardized, the description may be processed to extract one or more features of the food item from the description. In embodiments, these features may be extracted by converting tokens of the description into semantic feature vectors. This may be accomplished, for example, by first constructing a big feature vector, where each member of the big feature vector may correlate with a word appearing in the food and beverages database. In such an embodiment, a semantic feature vector may be constructed out of the description. The semantic feature vector may be the size of the big feature vector; however, only those members that correlate with words in the description may be marked as non-zero values. For example, if the description were simply "chicken sandwich" then the semantic feature vector for this description may be represented as (0, 0, 1, 0, 0, . . . , 1, 0) where the first "1" represents "chicken" and the second "1" represents "sandwich." The length of this semantic feature vector may be the same as that of the big feature vector discussed above, or one member per word contained in the food and beverages database. In addition, these 1s in a vector can be replaced by a data correlation scheme based on the relative importance of words. In some embodiments, this semantic feature vector may be normalized. For example, by squaring the numeric values of each token, summing the squared values, and then taking the square root of the sum to arrive at a normalized value. Such normalization may be beneficial to aid in giving food descriptions with varying lengths similar weight.

At block 206, the categorization engine may select one or more food categories based on a result of the analysis performed at block 204. In some embodiments, this selection may be based on the results of the feature extraction described above. In such embodiments, the extracted features of the description may be compared with a set of corresponding categorization features that have been determined to correlate with a food category. If a sufficient number of extracted features correspond with the categorization features of a food category, then that food category may be selected as one of the one or more food categories with which to associate the food item. In some embodiments, the above described process may continue until all food categories have been evaluated with respect to the extracted features and each food category that is determined to be within a predefined threshold of the extracted features may be selected as one of the one or more food categories. In other embodiments, only the category having the most categorization features in common with the extracted features may be selected as a food category with which to associate the food item. In other embodiments, this selection may be based on a mathematical combination and/or transformation between the extracted features and a semantic feature table. In such embodiments, the mathematical combination and/or transformation may be utilized to calculate the likelihood, or probability, that a food item belongs in each food category. For instance, for a certain food item, we may get features represented in a numerical vector such as, for example, x=(0.1, 4.1, . . . , 3.0) and the trained categorization engine may then utilize the semantic feature table, discussed further in reference to FIG. 3, below, represented by a matrix of numerical values, A, to compute the probability (or likelihood) that the food item belongs to each category. This may be accomplished, for example, through matrix-vector multiplication, A*x, where each outcome represents the probability of the respective food item belonging to each food category. It will be appreciated that the above examples are meant merely for illustration and are not meant to be limiting of this disclosure. Any mechanism capable of correlating extracted features of a food item description with one or more categories is contemplated.

At block 208, the categorization engine may establish an association of the food item with each of the one or more food categories. In some embodiments, such an association may be established through the addition of a unique identifier for each of the one or more categories to a category field, or table, associated with the food item in a food and beverages database (e.g., food and beverages database 114 of FIG. 1). In other embodiments, such an association may be established through the addition of a unique identifier for the food item to a food item field, or table, of each of the one or more food categories in the food and beverages database.

Figure 3:
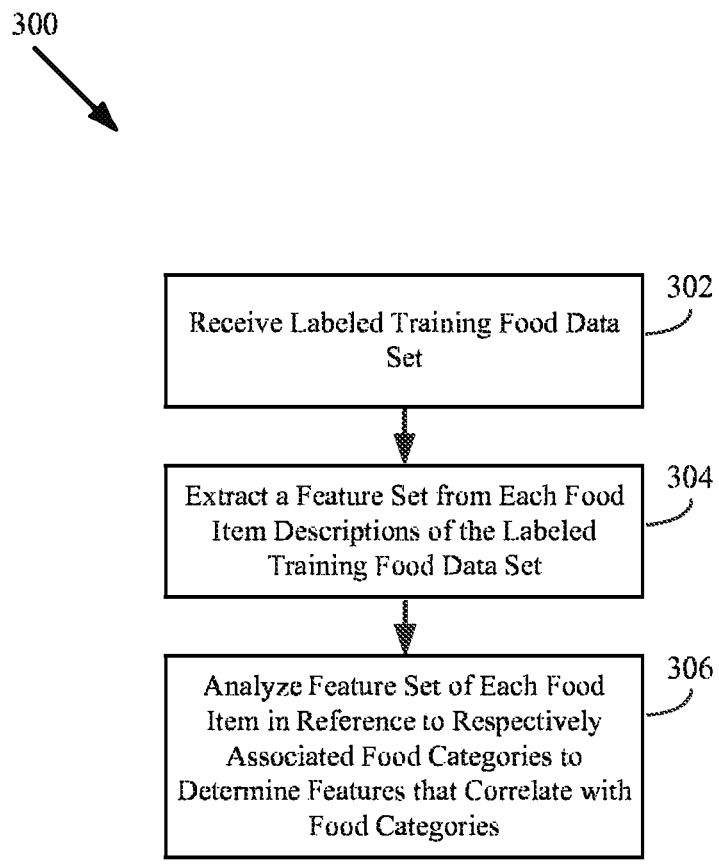
FIG. 3 illustrates an example operation flow for training a food item categorization engine with labeled food items, according to various embodiments.

FIG. 3 illustrates an example operation flow 300 for training a food item categorization engine (e.g., categorization engine 124 of FIG. 1), when operated in a training phase with labeled food items, in accordance with various embodiments. As used herein, a labeled food item may be a food item that has one or more food categories associated therewith. Such an associations may be entered by a user, as described in reference to FIG. 1, may be entered by a system administrator, or may be retrieved from a third-party reliable source, such as, for example, the food and drug administration (FDA).

Operation flow 300 may begin at block 302 where a labeled training food data set may be received by the categorization engine. Such a labeled training food data set may be received from a food and beverages database (e.g. food and beverages database 114 of FIG. 1) and may include any number of food items and respective descriptions along with an association of each of the food items with one or more food categories. In some embodiments, the labeled training food data set may be randomly selected from records stored within the food and beverages database. For example, an algorithm, such as a reservoir sampling algorithm, may be utilized in randomly selecting records from the food and beverages database. In addition, the labeled food data set may include records from any number of sources including, user supplied, or crowd-sourced, food items; food items entered by a system administrator; or food items pulled from a third-party reliable source, such as the FDA. In some embodiments, the labeled training food data set may be labeled by users through a series of questions that may be sent to the users by the categorization engine. The categorization engine may then label the food items with the appropriate category based on users' responses to the series of questions. In some embodiments, the series of questions may be binary questions where the answer involves a simple yes/no selection by the user. Such questions may reduce processing of the answers and may also improve the quality of the information that the answers to the questions provide by reducing the variability of possible answers. In some embodiments, upon receipt of the labeled food data set, the categorization engine may go through a standardization process, such as that described above in reference to FIG. 2, for each of the food items contained in the labeled food data set.

At block 304 the categorization engine may iterate through each of the food items and may extract a feature set of one or more features from the description of each food item in the labeled training food data set. The feature extraction process may be performed in a similar manner to that described above in reference to FIG. 2 to extract a feature set for each food item in the labeled training food data set.

At block 306, the feature set for each food item may be analyzed in conjunction with the label, or food categories, associated with the respective food item. As such, the categorization engine may be able to determine features that correlate with individual food categories. From this correlation the categorization engine may generate a distributional semantic model, such as a semantic feature table, that may be a data structure representation of the correlation between feature sets of each food item and the one or more categories associated with the respective food item.

Figure 4:
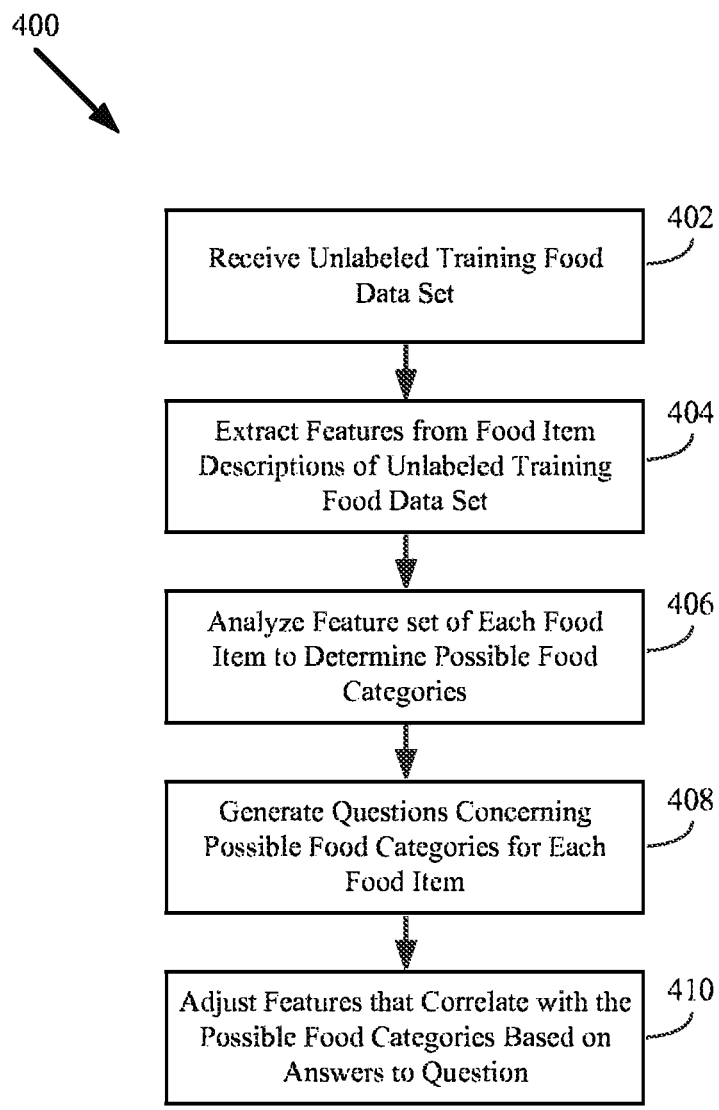
FIG. 4 illustrates an example operation flow for training a food item categorization engine with unlabeled food items, in accordance with various embodiments.

FIG. 4 illustrates an example operation flow 400 for training a food item categorization engine in a training phase with unlabeled food items, in accordance with various embodiments. Operation flow 400 may begin at block 402 where an unlabeled training food data set may be received by the categorization engine. Such an unlabeled training food data set may be received from a food and beverages database (e.g. food and beverages database 114 of FIG. 1) and may include any number of food items and respective descriptions. In some embodiments, the unlabeled training food data set may be randomly selected from records within the food and beverages database. In addition, the unlabeled food data set may include records from any number of sources including, user supplied, or crowd-sourced, food items; food items entered by a system administrator; or food items pulled from a third-party reliable source, such as the FDA. In some embodiments, upon receipt of the unlabeled food data set, the categorization engine may go through a standardization process for each of the food items contained in the labeled food data set, such as that described above in reference to FIG. 2.

At block 404 the categorization engine may iterate through each of the food items and may extract a feature set of one or more features from the description of each food item in the unlabeled training food data set. The feature extraction process may begin by tokenizing the description of each food item, if not already performed in a standardization process. In some embodiments, the feature sets may be extracted by converting unique tokens of each description into numeric values. The numeric values may form a semantic feature vector for each token which may then be summed resulting in a vector sum representing the feature set for each description. In some embodiments, this vector sum may be normalized, as discussed in reference to FIG. 2.

At block 406, the categorization engine may analyze the feature set of each food item to determine one or more possible food categories for each food item of the unlabeled training food data set. In embodiments, such an analysis may be based on a result of the feature extraction performed at block 404. In such embodiments, the extracted features of the description may be compared with a set of corresponding categorization features, such as those represented by a semantic feature table, as discussed above, that have been determined to correlate with a food category. If a sufficient number of extracted features correspond with the categorization features of a food category, then that food category may be selected as one of the one or more possible food categories with which to associate the food item. In some embodiments, the above described process may continue until all food categories have been evaluated with respect to the extracted features and each food category that is determined to be within a predefined threshold of the extracted features may be selected as one of the one or more possible food categories. In other embodiments, only the category having the most categorization features in common with the extracted features may be selected as a possible food category with which to associate the food item.

At block 408, the categorization engine may generate one or more questions associated with the one or more possible food categories to be sent to one or more users. Such questions may include binary, yes/no, questions. For example, a question for each of the one or more possible food categories may be whether a user thinks the food item belongs in each of the one or more possible food categories to which the user may either respond in the affirmative or the negative.

At block 410, the features that caused each food item to be associated with the one or more possible categories may be adjusted based on the answers the user provides to the one or more questions to fine tune the categorization. For example, where a particular feature set caused the categorization engine to determine that a food item belonged to a specific food category, a negative answer to the above discussed questions may decrease a weight, or priority, of one or more of the features in the feature set, while an affirmative answer may increase the weight, or priority, of the one or more features.

Figure 5:
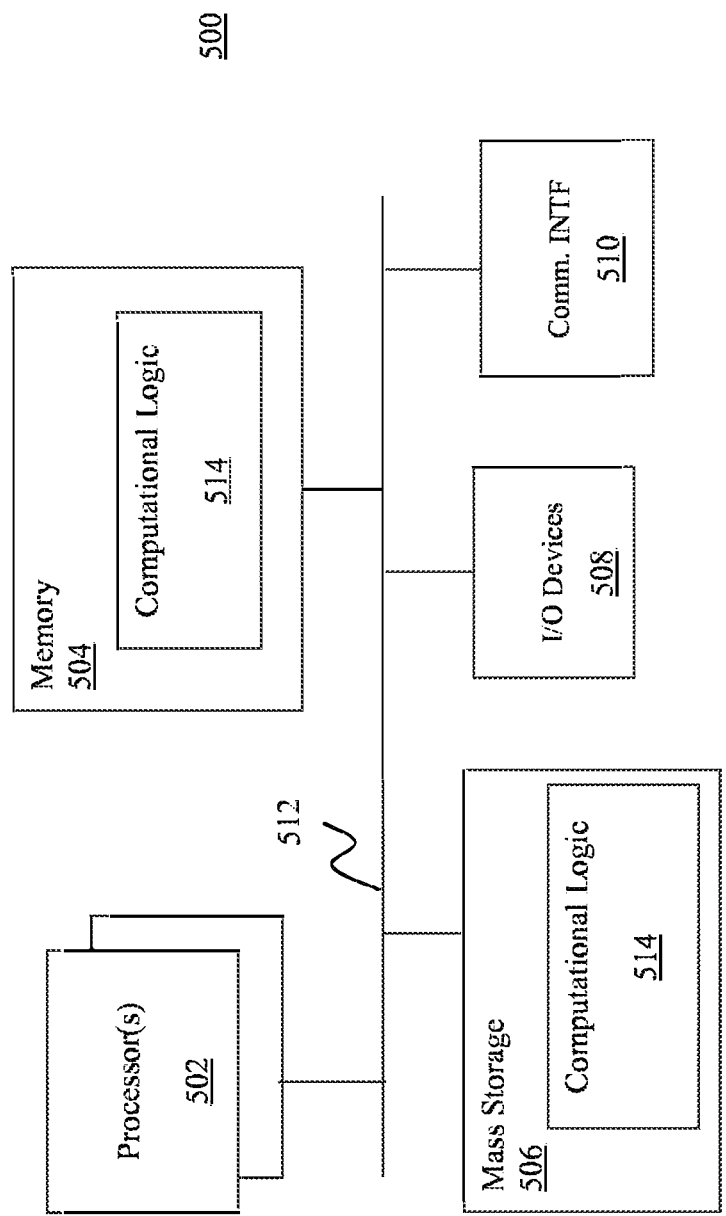
FIG. 5 illustrates an example computing system suitable for use as a server computing device or a client computing device, in accordance with various embodiments.

Referring now to FIG. 5, wherein an example computer suitable for use as server(s) 104 or client device 102 of FIG. 1, in accordance with various embodiments, is illustrated. As shown, computer 500 may include one or more processors or processor cores 502, and system memory 504. For the purpose of this application, including the claims, the terms "processor" and "processor cores" may be considered synonymous, unless the context clearly requires otherwise. Additionally, computer 500 may include mass storage devices 506 (such as diskette, hard drive, compact disc read only memory (CD-ROM) and so forth), input/output devices 508 (such as display, keyboard, cursor control and so forth) and communication interfaces 510 (such as network interface cards, modems and so forth). The elements may be coupled to each other via system bus 512, which may represent one or more buses. In the case of multiple buses, the buses may be bridged by one or more bus bridges (not shown).

Each of these elements may perform its conventional functions known in the art. In particular, when used as server(s) 104, system memory 504 and mass storage devices 506 may be employed to store a working copy and a permanent copy of the programming instructions implementing the operations associated with fitness management application 112 and categorization engine 124 of FIG. 1, above, collectively referred to as computational logic 522. The various elements may be implemented by assembler instructions supported by processor(s) 502 or high-level languages, such as, for example, C, that can be compiled into such instructions.

The permanent copy of the programming instructions may be placed into permanent storage devices 506 in the factory, or in the field, through, for example, a distribution medium (not shown), such as a compact disc (CD), or through communication interface 510 (from a distribution server (not shown)). That is, one or more distribution media having an implementation of the agent program may be employed to distribute the agent and program various computing devices.

The number, capability and/or capacity of these elements 510-512 may vary, depending on whether computer 500 is used as server(s) 104 or client device 102. When used as client device 102, computing device 500 may be a smartphone, computing tablet, e-reader, ultrabook, or laptop. Otherwise, the constitutions of elements 510-512 are known, and accordingly will not be further described.

FIG. 6 illustrates an example computer-readable non-transitory storage medium having instructions configured to practice all or selected ones of the operations associated with earlier described fitness management application 112 and/or categorization engine 124 of FIG. 1, in accordance with various embodiments. As illustrated, non-transitory computer-readable storage medium 602 may include a number of programming instructions 604. Programming instructions 604 may be configured to enable a device, e.g., computer 600, in response to execution of the programming instructions, to perform, e.g., various operations of the processes described above in reference to FIGS. 1-4, e.g., but not limited to, the operations associated with categorization engine 124. In alternate embodiments, programming instructions 604 may be disposed on multiple computer-readable non-transitory storage media 602 instead. In alternate embodiments, programming instructions 604 may be disposed on computer-readable transitory media 602, such as, signals.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method comprising:
receiving, by a food categorization engine provided on a server and operating in a training mode, a training food data set including a plurality of text descriptions of a plurality of food items and a corresponding association of each of the plurality of food items of the training food data set with one or more food categories of a plurality of food categories, wherein the training food data set is provided from a database of crowd-sourced data records of food items;
extracting, by the food categorization engine, one or more features from each text description of the training food data set to generate a feature set for each food item of the training food data set;
analyzing, by the food categorization engine, the feature set for each food item of the training food data set to determine sets of food categorization features that correlate to individual ones of the one or more food categories, wherein the sets of food categorization features are defined by a plurality of category vectors, each of the category vectors associated with one of the food categories;
standardizing a text description of a food item received from a user of a client device in communication with the server, the food item associated with a data record in the database;
analyzing, by the food categorization engine, one or more individual words and/or characters of the text description of the food item, wherein analyzing the one or more individual words and/or characters of the text description of the food item comprises generating a numerical vector representative thereof;
multiplying the numerical vector by a matrix defined by the plurality of category vectors, wherein said multiplication produces a resulting vector indicative of probabilities that the received food item belongs in each of the plurality of food categories;
automatically selecting one or more food categories of the plurality of food categories to associate the food item based at least in part on the probabilities indicated by the resulting vector; and amending the data record associated with the food item in the database to include the selected one or more food categories.

2. The method of claim 1, further comprising:
selecting the amended data record based on the one or more food categories; and
transmitting data from the amended data record to the user for display on the client device.

3. The method of claim 1 further comprising:
establishing, by the food categorization engine, one or more associations of the food item with the one or more food categories in a food data storage arrangement of a fitness management system, wherein the food categories are food nutrient categories, and wherein each of the data records are entered by users of the fitness management system;
wherein the act of establishing the one or more associations comprises one or more of:
adding one or more text identifiers descriptive of the one or more categories to a category field associated with the text description of the food item; and
adding an identifier from the text description of the food item to a food item field of each of the one or more food categories.

4. The method of claim 1, wherein the act of standardizing comprises removing nonstandard words and/or characters from the one or more individual words and/or characters of the text description of the food item further and includes one or more of:
removing non-English characters from the one or more individual words and/or characters of the text description of the food item;
removing numeric words from the one or more individual words and/or characters of the text description of the food item;
removing words related to quantities from the one or more individual words and/or characters of the text description of the food item;
removing punctuations from the one or more individual words and/or characters of the text description of the food item; and
removing special characters from the one or more individual words and/or characters of the text description of the food item.

5. The method of claim 1, wherein:
the act of analyzing the one or more individual words and/or characters of the text description of the food item comprises extracting one or more features of the food item from the text description; and
the act of selecting the one or more food categories with which to associate the food item is based at least in part on the extracted features.

6. The method of claim 1 wherein the training food data set is a first training food data set, the method further comprising:
receiving, by the food categorization engine, a second training food data set including a second plurality of text descriptions of a second plurality of food items, the second training food data set omitting corresponding associations thereof with one or more of the plurality of food categories;
extracting, by the food categorization engine, one or more features from each text description of the second training food data set in order to generate a feature set for each food item of the second training food data set; and
analyzing, by the food categorization engine, the feature set for each food item of the second training food data set to identify one or more possible food categories therefor based at least in part on a common set of one or more features that correlate to individual ones of the one or more food categories.

7. The method of claim 6, further comprising:
generating a series of questions concerning the one or more possible food categories identified for each food item of the second training food data set; and
adjusting the common set of one or more features based on answers for the series of questions received from one or more of a plurality of users.

8. The method of claim 1 wherein the matrix is representative of a semantic feature table and the numerical vector is representative of features of the food item.

9. One or more non-transitory computer-readable media having a plurality of instructions stored thereon, the instructions, in response to execution by a processor of a network-side computing device in communication with a crowd-sourced database of data records of food items, provide the computing device with a food item categorization engine operable to:
receive, in a training mode, a training food data set including a plurality of text descriptions of a plurality of food items and a corresponding association of each of the plurality of food items of the training food data set with one or more food categories of a plurality of food categories;
extract one or more features from each text description of the training food data set to generate a feature set for each food item of the training food data set;
analyze the feature set for each food item of the training food data set to determine sets of food categorization features that correlate to individual ones of the one or more food categories, wherein the sets of food categorization features are defined by a plurality of category vectors, each of the category vectors associated with one of the food categories;
receive, in an operational mode, a data record including a text description of a food item from a client-side application configured to log consumption of food items, wherein the received data record is selected by the user as being indicative of a consumed item, the data record being provided from the database of crowd-sourced data records of food items;
standardize the text description of the food item included with the received data record;
analyze one or more individual words and/or characters of the text description of the food item to create a numerical vector representative thereof;
automatically select one or more food categories with which to associate the received data record and associated food item based at least in part on a result of a comparison of the numerical vector to the plurality of category vectors associated with individual ones of the one or more food categories, wherein the comparison is accomplished by matrix-vector multiplication wherein the plurality of category vectors associated with individual ones of the one or more food categories define a matrix that is multiplied by the numerical vector to produce a resulting vector indicative of probabilities that the received food item belongs in each of the plurality of food categories;
amend the data record associated with the food item in the database to include the automatically selected one or more food categories; and
select the amended data record based on the one or more food categories.

10. The computer-readable media of claim 9, wherein the food item categorization engine is further configured to store the numerical vector with a plurality of numerical vectors associated with the individual ones of the one or more food categories in a food data storage arrangement of a fitness management system.

11. The computer-readable media of claim 9, wherein the food item categorization engine is further configured to:
add one or more identifiers of the respective one or more categories to a category field of the data record of the food item; and
add an identifier of the food item to a food item field of a data record of each of the one or more food categories.

12. The computer-readable media of claim 9,
wherein the analysis of the text description further comprises extraction of one or more features from the numerical vector of the food item; and
wherein the food item categorization engine is further configured to select the one or more food categories with which to associate the food item based at least in part on the features extracted from the numerical vector of the food item.

13. The computer-readable media of claim 9, wherein the food item categorization engine is further configured to:
transmit an association of the data record for the food item and the selected one or more food categories to the client-side application thereby enabling the application to indicate in said logged consumption of food items a quantity of consumption in each of a plurality of food categories.

14. The computer-readable media of claim 9 wherein comparison of the numerical vector to a plurality of category vectors comprises, identification of one of the plurality of food categories associated to one of the plurality of category vectors to which the numerical vector matches within a predetermined threshold.

15. A server apparatus, comprising:
at least one transceiver;
a storage apparatus configured to store a plurality of instructions of a food categorization engine; and
one or more processors configured to execute the plurality of instructions of the food categorization engine, which when executed cause the server apparatus to:
receive, in a training mode, a training food data set including a plurality of text descriptions of a plurality of food items and a corresponding association of each of the plurality of food items of the training food data set with one or more food categories of a plurality of food categories, the training food data set provided from a database of crowd-sourced data records of food items entered into the database by a plurality of users of a fitness management system;
extract one or more features from each text description of the training food data set to generate a feature set for each food item of the training food data set;
analyze the feature set for each food item of the training food data set to determine sets of food categorization features that correlate to individual ones of the one or more food categories, wherein the sets of food categorization features are defined by a plurality of category vectors, each of the category vectors associated with one of the food categories;
receive, in an operational mode, at the transceiver an input from a client device comprising a data record including a description of a food item, wherein the received data record is indicative of a consumed item, the data record being provided from the database of crowd-sourced data records;
standardize the description of the food item to create a plurality of tokens representative of one or more individual words and/or characters thereof;
convert the plurality tokens to a numerical vector;
compare the numerical vector to a plurality of sets of the plurality of category vectors, each set being associated to a respective one of a plurality of food categories, wherein said comparison is accomplished by matrix-vector multiplication wherein the plurality of category vectors define a matrix that is multiplied by the numerical vector to produce a resulting vector indicative of probabilities that the received food item belongs in each of the plurality of food categories;
based on the comparison and the resulting probabilities, identify a one of the plurality of food categories associated to a one of the plurality of sets of the plurality of category vectors to which the numerical vector matches within a predetermined threshold;
amend the data record to include the identified one of a plurality of food categories, the data record associated with the description of the food item in the database; and
select the amended data record from the database based on the identified one of the plurality of food categories.

16. The server apparatus of claim 15, wherein the execution of the food categorization engine further causes the server apparatus to:
transmit data from the amended data record and the identified one of the plurality of food categories to the client device via the at least one transceiver, the client device configured to run at least one fitness management application thereon which is configured to utilize the identified one of the plurality of food categories in a running log of a user's consumption across each of the plurality of food categories during a time period.

17. The server apparatus of claim 15, wherein the one or more processors are further configured to execute a plurality of instructions of a network-side fitness management application, which when executed causes the server apparatus to:
utilize the identified one of the plurality of food categories in a running log of a user's consumption across each of the plurality of food categories during a time period; and
cause the at least one transceiver apparatus to transmit the running log to a client-side fitness management application run at the client device.

18. The server apparatus of claim 15, wherein the execution of the food categorization engine further causes the server apparatus to:
process the tokens via removal of nonstandard words and/or characters therefrom.

19. The server apparatus of claim 15, wherein the execution of the food categorization engine further causes the server apparatus to:
associate the description of the food item to the identified one of the plurality of food categories by placing the numerical vector in the one of the plurality of sets of the plurality of category vectors.

20. The server apparatus of claim 15, wherein the one or more processors are further configured to execute a plurality of instructions of a food categorization engine training application, which when executed causes the server apparatus to: generate the plurality of sets of the plurality of category vectors for each of the plurality of food categories.

21. The server apparatus of claim 20, wherein the execution of the food categorization engine training application generates the plurality of sets of the plurality of category vectors for each of the plurality of food categories by causing the server apparatus to:
- receive a plurality of training data from a plurality of client devices in communication with the server apparatus, each of the plurality training data comprising at least a description of a food item and a corresponding association of the food item to one or more of the plurality of food categories;
- for each of the plurality of training data, standardize the description of the food item to create a plurality of tokens representative of one or more individual words and/or characters thereof;
- convert the plurality tokens associated with each of the plurality of training data to a numerical vector; and
- place individual ones of the numerical vectors into one or more of the plurality of sets of a plurality of category vectors based on the associations in the training data.

* * * * *